United States Patent [19]
Woodson

[11] Patent Number: 5,165,387
[45] Date of Patent: Nov. 24, 1992

[54] ENDOSCOPE WITH DISPOSABLE LIGHT
[75] Inventor: David Woodson, Spartanburg, S.C.
[73] Assignee: Transidyne General Corporation, Spartanburg, S.C.
[21] Appl. No.: 650,228
[22] Filed: Feb. 4, 1991
[51] Int. Cl.$^5$ ................................................ A61B 1/06
[52] U.S. Cl. ........................................................ 128/6
[58] Field of Search .................. 128/3, 4, 6, 9, 7, 11, 128/18

[56] References Cited

U.S. PATENT DOCUMENTS

| | | | |
|---|---|---|---|
| 1,286,083 | 11/1918 | Pennington | 128/6 |
| 1,556,355 | 10/1925 | Roney | 128/6 |
| 3,075,516 | 1/1963 | Strauch | 128/6 |
| 3,373,736 | 3/1968 | Fiore et al. | 128/6 |
| 3,592,199 | 7/1971 | Ostensen | 128/11 |
| 3,685,509 | 8/1972 | Bentall . | |
| 3,769,968 | 11/1973 | Blount et al. | 128/6 |
| 4,046,140 | 9/1977 | Born . | |
| 4,207,872 | 6/1980 | Meiri et al. | 128/4 |
| 4,219,013 | 8/1980 | Okada | 128/4 |
| 4,350,147 | 9/1982 | Sarrine | 128/4 |
| 4,449,519 | 5/1984 | Sarrine | 128/4 |
| 4,546,761 | 10/1985 | McCullough | 128/6 |
| 4,561,430 | 12/1985 | Walsh | 128/6 |
| 4,766,886 | 8/1988 | Juhn | 128/9 |

FOREIGN PATENT DOCUMENTS 361581  11/1931  United Kingdom ................. 128/3

OTHER PUBLICATIONS

Mueller & Co. Catalog No. 65 "A Comprehensive Guide To Purchasing" Mar. 1963.

Primary Examiner—Gene Mancene
Assistant Examiner—Todd E. Manahan
Attorney, Agent, or Firm—Krass & Young

[57] ABSTRACT

A disposable endoscope kit 10 has a speculum member 22 and a disposable light source 24. The light source includes a battery 48 and a light bulb 46 mounted within a housing 44. The housing 44 is a clip mounted onto the tubular wall 36 of speculum member 22 in proximity to the proximal viewing end 28. The housing 44 is mounted substantially within the speculum member 22 between the proximal viewing end 28 and the distal insertable end 26. The light source 24 has a switch 50 which is activated when the light source 24 is mounted to the speculum 22 to direct light toward end 26.

14 Claims, 2 Drawing Sheets

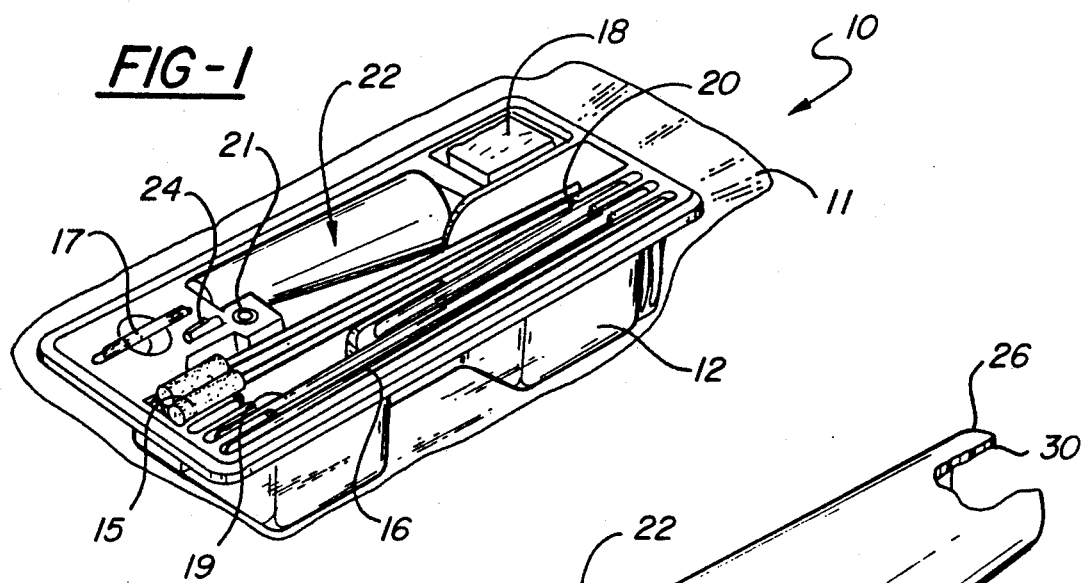
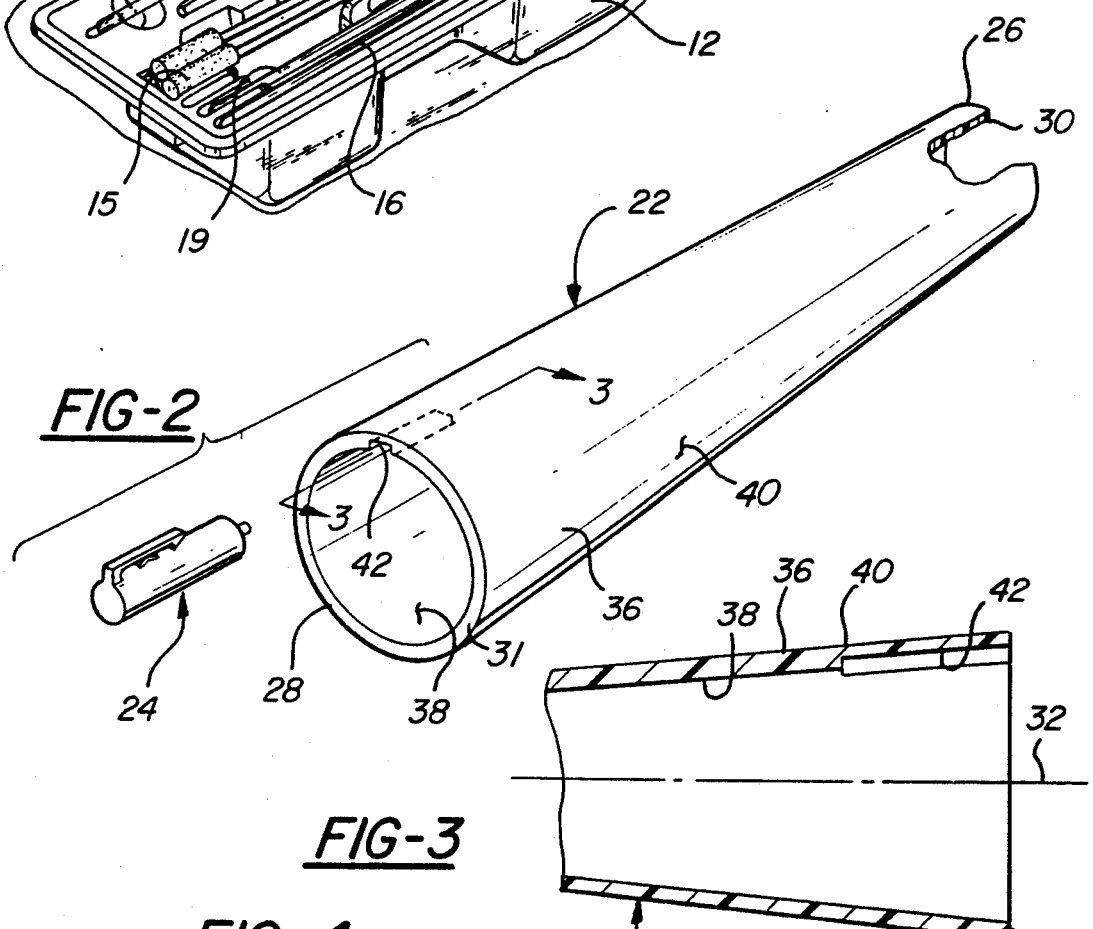
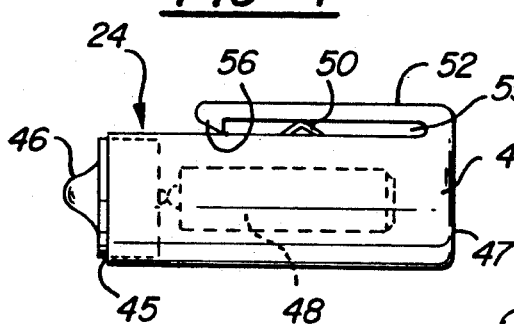
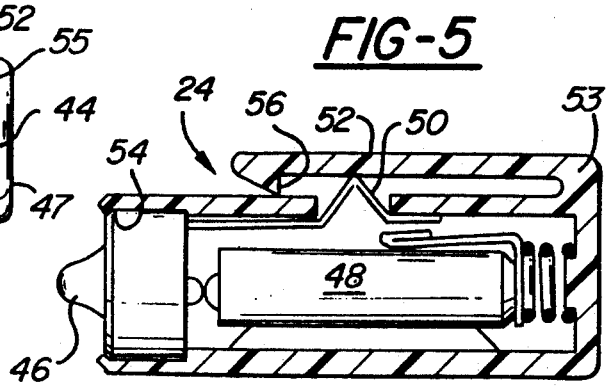

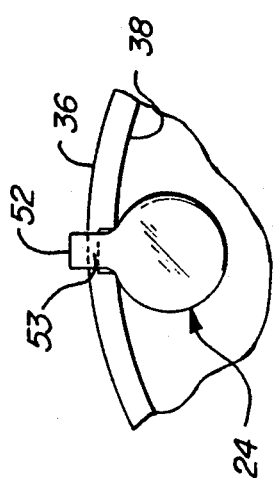
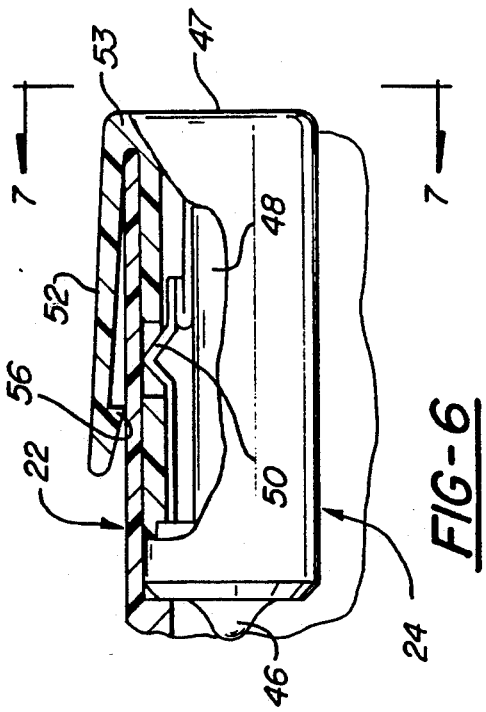
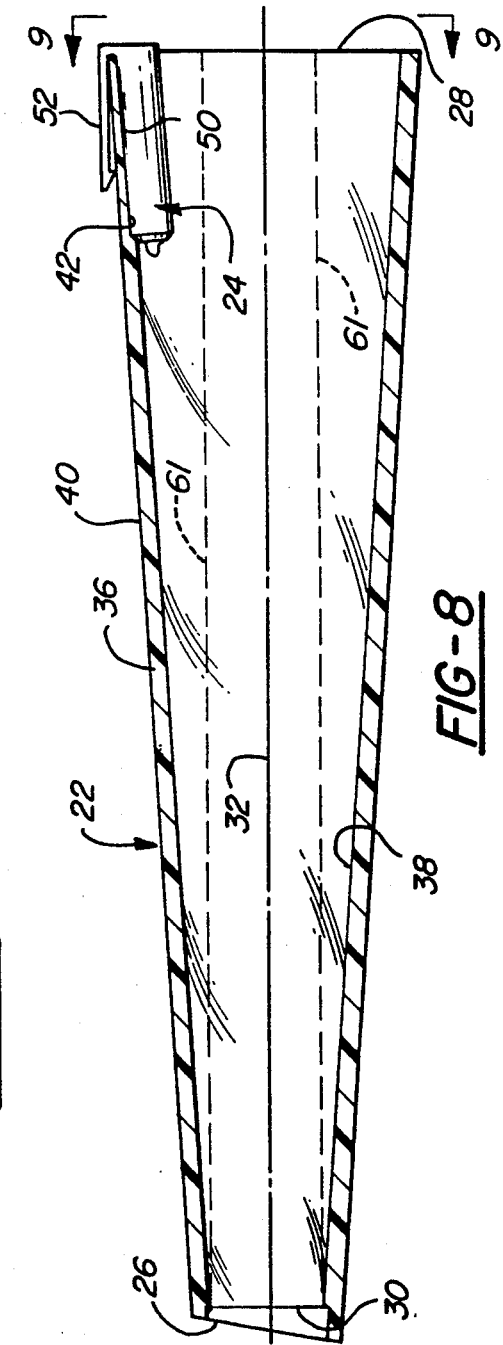

5,165,387

ENDOSCOPE WITH DISPOSABLE LIGHT

TECHNICAL FIELD

This invention relates generally to medical instruments and more particularly to endoscopes having a light source for inspection through a vagina.

BACKGROUND OF THE INVENTION

Endoscopes have long been used to examine for tumors and other abnormal conditions. They can also be used to examine a developing fetus through the vagina. For adequate inspection and examination, proper illumination is required. A light source is needed to transmit light through the endoscope through the distal insertable end thereof. Light sources have been attached onto a stand mounted behind the endoscope with the light directed into the endoscope. Mirror assemblies can also be mounted to the stand to allow for self-examination. One such example is shown in U.S. Pat. No. 3,075,516 issued to C. B. Strauch on Jan. 29, 1963. The light source and mirror assembly mounted behind the endoscope is particularly suited for self-examination but becomes an obstacle for a doctor or a second person to view directly into the endoscope.

Endoscopes provided for use by a doctor or second person have a sleeve member attached to an inner wall of the endoscope to mount a high intensity halogen bulb which is powered through a flexible power cord operably connected to a remote medical battery pack. Alternatively, the bulb can be replaced with a fiber optic tube which transmits light from a remote powered light source.

What is needed is a cordless endoscope having a sterilized, self-contained light assembly mountable within the endoscope. Further what is needed is a sterilized examination kit containing a sterilized speculum and a sterilized light source that can be assembled together without the need for wires or other connections to a remote power source.

SUMMARY OF THE INVENTION

In accordance with one aspect of the invention, a disposable endoscope kit includes a speculum and a self-contained light source which is mountable within the speculum. The light source includes a switch and a power source mounted in a housing. The light source is provided with an activation means for activating the power source. Preferably, the activation means is a switch that is automatically turned on when the light source is mounted to the speculum.

In one embodiment, the speculum has a frusto-conical wall having a distal insertable end and a proximal viewing end. A groove is in an interior wall surface adjacent the viewing end. The groove slidably receives a ridge longitudinally extending along the light source housing. The light source housing has an integral clip member. A slot is formed between the clip and housing for receiving the speculum such that the clip axially extends along the outer surface of the speculum wall above the ridge. A distal end of the clip has a tooth that engages the exterior wall surface of the speculum and resists any motion to disengage the light source from the speculum wall.

The switch member is preferably positioned under the clip and is operably engageable against the speculum wall when the speculum wall is received in the slot interposed between the clip and the light source housing. In one embodiment, the light source housing is substantially cylindrical and sized to receive a AA size battery. The light source housing is mounted on the speculum such that its longitudinal axis is substantially parallel to the speculum wall to which it is mounted. The light source is mounted at one end of the housing and points toward the distal insertable end of the speculum. In one embodiment the speculum is tapered and the light source is mounted at the larger end of the speculum such that it is positioned outside the periphery of a projection of the smaller end opening, the projection being along the longitudinal axis of the speculum.

In this fashion, a wireless portable endoscope has a self-contained light source. Furthermore, the endoscope and light source can be easily packaged as part of a sterilized kit. The longitudinal position of the light source presents minimal interference with the inspecting and examining through the viewing end of the speculum. Furthermore, the light source and speculum are disposable which eliminates the need for repeated sterilization of a light source connected to a speculum.

BRIEF DESCRIPTION OF THE DRAWINGS

Reference now is made to the accompanying drawings in which:

FIG. 1 is a perspective view of a kit assembly according to one embodiment of the invention;

FIG. 2 is a perspective view of the speculum and light source shown in FIG. 1;

FIG. 3 is a fragmentary cross-sectional view of the speculum taken along lines 3—3 shown in FIG. 2;

FIG. 4 is a side elevational view of the light source member;

FIG. 5 is a side-elevational, partially segmented view of the light source member shown in FIG. 4;

FIG. 6 is a fragmentary and partially segmented view similar to FIG. 3 illustrating the light source mounted to the speculum;

FIG. 7 is an end view taken along the lines 7—7 shown in FIG. 6;

FIG. 8 is a partially segmented view illustrating the position of the light source in the speculum; and FIG. 9 is an end view taken along lines 9—9 shown in FIG. 8.

DETAILED DESCRIPTION OF THE PREFERRED EMBODIMENT

FIG. 1 discloses an endoscope kit 10 with a sealed wrapping 11 (shown transparent for illustrative purposes). The kit 10 with the sealed wrapping 11 contains apparatus and supplies for an medical examination through a vagina. The kit 10 components within the sealed wrapping 11 are a tray 12, an optional disposable sheet (not shown), a plurality of swabs 15, long capillary tubes 16, short capillary tubes 17, silicone gel 18, scalpel 19, prong 20, capillary tube sealant 21, a speculum 22, and a light source member 24. The speculum 22 and light source member 24 are connectable together as described in further detail below.

Referring to FIGS. 2 and 3, the speculum member 22 has a frusto-conical tubular wall member 36 made from a white injection molded plastic. The speculum 22 has a distal insertable end 26 and a proximal viewing end 28. The proximal viewing end 28 is significantly larger than the insertable end 26. The proximal end 28 has its annular end shoulder 31 perpendicular to a longitudinal axis 32 of the speculum 22. Furthermore, the insertable end 26 has its annular end shoulder 30 canted with respect to the longitudinal axis 32. The frusto conical tubular wall 36 defining the speculum 22 has an interior surface 38 and an exterior surface 40. The interior surface 38 has a slot 42 extending longitudinally from end shoulder 31 of proximal end 28 and toward the insertable end 26.

The light source member 24 as shown in FIGS. 4 and 5 includes a generally cylindrical shaped housing 44 sized to receive a battery 48 such as a AA size tubular battery. One end of the housing 44 mounts a high intensity light bulb 46. The light bulb 46 either screws into the open end 45 of housing 44 or can have a retaining collar which snaps into the housing open end 45. It is desirable that the light bulb 46 is rated to run on 1.5 volts and can operate for 45 to 60 minutes off of battery 48. Of course, if future smaller battery sources are available, the housing 44 can be decreased in size to accommodate a smaller battery. If additional power is needed, a second battery can be included. The second battery may be mounted adjacent the exterior surface 40. Alternatively, the battery pack may be positioned adjacent the exterior surface between the two ends and operably connected to the bulb adjacent the inner surface. The housing 44 also incorporates a switch mechanism 50 and a clip 52 which is integrally formed with housing 44. The housing 44 and clip 52 can be formed by plastic injection.

On the outside of the housing 44 is a longitudinally extending ridge 54 which is sized in height, length and width to be received in slot 42. The clip member 52 has a bent mounting end 53 radially extending from the closed end 47 of housing 44. A tooth 56 located at the distal end of clip 52 points to housing 44. The clip 52 longitudinally extends along the cylindrical housing 44 and forms a slot 55 therebetween. The tooth 56 engages the exterior surface 40 of tubular wall 46 when the speculum is inserted in slot 55 as illustrated in FIGS. 6 and 8 such that it provides resistance against disengaging motion exerted on the light source member 24. The clip 52 also provides a spring bias such that it retains the housing 44 against the interior surface 38 and ridge 54 within slot 42. The ridge 52 and slot 42 provides for the longitudinal alignment of the housing 44 with the speculum wall 36 and resistance against relative lateral rotation as shown in FIG. 7.

The switch member 50 protrudes through the housing 44 positioned through ridge 54 lying under clip 52 such that insertion of the tubular wall 36 in slot 55 between the clip 52 and housing 44 automatically closes the switch 50 to provide power to the light bulb 46 from the battery 48. Alternatively the housing 44 can be made from a flexible plastic material such that the switch 50 can be operably mounted through the housing 44 without having an exposed portion protruding therethrough. Other types of automatically actuated switches such as magnetic switches are foreseen to be suitable for the present application. Preferably the light source, including housing 44, battery 48, and bulb 46 can be irradiated to a minimum of 4 m rad for sterilization purposes without degradation of performance. The color of the housing is also preferred to be white to match the white speculum member 22.

As shown in FIGS. 8 and 9, the assembled endoscope with its disposable light source provides an unobstructed view through the proximal viewing end 28 to the insertable distal end 26. The light source 24 is mounted radially outside of the periphery of projection 61 taken along the longitudinal axis 32 of open distal end 26. The light bulb 46 pointed toward end 26 illuminates the examination area such that observations can be made through the endoscope. As illustrated in FIGS. 8 and 9 the light source 24 is substantially within the confines of the speculum member 22. Furthermore, there are no wires protruding from the endoscope assembly 25 that would restrict its motion or portability.

Alternatively, shoulder 31 may have a notch therein aligned with slot 42 such that clip end 53 may be recessed in said notch and provide that the housing 44 is completely within the axial confines of speculum 22. Another modification that is foreseen is a single activated switch mounted in housing 44 that remains on when activated.

After single use of the endoscope assembly 25, the assembly 25 with the light source and kit 10 are discarded. Each endoscopic procedure uses a new sterilized kit 10 with its own sterilized light source. Thus, the need to separately sterilize a reusable light source which is connectable to a speculum is eliminated.

Variations and modifications of the preferred embodiment are possible without departing from the spirit and scope of the invention as defined by the appended claims.

The embodiments in which the exclusive property or privilege is claimed are defined as follows:

1. An endoscope comprising:
   a unitary tubular speculum having a tubular wall member tapering from a larger open proximal viewing end down to a smaller, open and distal end;
   a portable light source housing containing a power source for producing light and being mountable in said tubular speculum for directing light to said distal end;
   said tubular wall member having an interior surface and a mounting means for mounting said light source housing thereon;
   said light source housing having a switch thereon for activating said power source when said light source housing is mounted on said mounting means; and
   said light source housing being mounted radially outboard of a central, longitudinal, axial projection of the smaller distal end such that said housing does not obstruct a line of sight through said projection.

2. An endoscope as defined in claim 1 wherein:
   said switch is normally in an off position and is automatically activated when said light source is mounted said mounting on means.

3. An endoscope as defined in claim 1 wherein:
   said light source housing is mounted on said tubular wall member at said proximal viewing end and substantially mounted within said speculum between said proximal and distal ends thereof.

4. An endoscope as defined in claim 1 wherein said light source housing is mounted in proximity to said proximal viewing end.

5. An endoscope comprising:
   a tubular speculum having a tubular wall member with an open proximal viewing end and open distal end;
   a portable light source housing containing a power source for producing light and being mountable in said tubular speculum for directing light to said distal end;
   said tubular wall member having an interior surface mounting means for mounting said light source housing thereon at said proximal viewing end and substantially within said speculum between said proximal and distal ends thereof;

said light source housing having a switch thereon for activating said power source when said light source housing is mounted on said mounting means;

said mounting means including a slot on an interior surface of said tubular wall member at said proximal viewing end and longitudinally extending toward said distal end;

said light source housing having a longitudinally extending ridge sized to fit in said slot and a clip longitudinally extending along said ridge; and said tubular wall at said slot being interposed between said ridge and said clip.

6. An endoscope as defined in claim 5 wherein:

said clip has a distal toothed end for engaging an outer surface of said tubular wall member of said speculum such that it provides resistance against disengaging motion of said light source housing out from said proximal end of said speculum.

7. An endoscope as defined in claim 6 wherein:

said speculum is frusto-conical in shape with said open distal end being smaller than said proximal end.

8. An endoscope as defined in claim 7 wherein:

said light source housing is mountable substantially within said speculum and radially outside of a projection of said open distal end, said projection being along a central longitudinal axis of said speculum.

9. An endoscope as defined in claim 7 wherein:

said switch is positioned on said light source housing such that said switch is activated by said speculum member when it is interposed between said clip and said switch.

10. An endoscope as defined in claim 9 wherein:

said light source housing is a plastic housing mounting a light bulb, said power source, and said switch; said power source is a battery and said clip is integrally formed with said housing.

11. An endoscope assembly comprising:

a unitary tubular frusto-conical speculum having an open proximal end and an open distal end, said distal end being smaller than said proximal end;

a light radiating source mounted in said tubular speculum for directing light toward said distal end;

a power means for said light radiating source mounted onto said speculum substantially between said ends;

said power means and light radiating source being mounted radially outboard of a central, longitudinal, axial projection of the smaller distal end such that said projection does not obstruct a line of sight through said projection.

12. An endoscope as defined in claim 11 wherein:

said power means is mounted substantially within said tubular speculum.

13. An endoscope as defined in claim 12 wherein:

said light source is mounted in proximity to said proximal viewing end.

14. A disposable endoscope kit comprising:

a sealed package containing a sterilized tapered, unitary speculum and a sterilized self-powered light source; said light source being mountable within said speculum so as not to obstruct a line of sight along the length of the speculum from a viewing end thereof and activatable when mounted to said speculum for directing light to one end of said speculum.

* * * * *